United States Patent [19]
Hodges

[11] Patent Number: 5,636,388
[45] Date of Patent: Jun. 10, 1997

[54] GOGGLES

[76] Inventor: Robert Hodges, 320-1/2 Swanson Rd., Saginaw, Mich. 48609

[21] Appl. No.: 364,739

[22] Filed: Dec. 27, 1994

[51] Int. Cl.[6] .................................................. A61F 9/02
[52] U.S. Cl. ............................. 2/443; 2/452; 2/454
[58] Field of Search .......................... 2/452, 453, 454, 2/441, 443, 426, 431, 432, 439, 440

[56] References Cited

U.S. PATENT DOCUMENTS

| | | | |
|---|---|---|---|
| 2,388,635 | 11/1945 | Ditto | 2/441 |
| 3,009,158 | 11/1961 | Comeau et al. | 2/453 |
| 3,173,147 | 3/1965 | Gross et al. | 2/452 |
| 3,373,444 | 3/1968 | Militello | 2/453 X |
| 3,378,851 | 4/1968 | McBrayer | 2/452 |
| 3,689,136 | 9/1972 | Atamian | 351/44 |
| 3,808,604 | 5/1974 | Rose | 2/10 |
| 4,520,510 | 6/1985 | Daigle | 2/452 |
| 4,616,367 | 10/1986 | Jean, Jr. et al. | 2/452 |
| 4,686,712 | 8/1987 | Spiva | 2/10 |
| 4,689,838 | 9/1987 | Angermann et al. | 2/441 |
| 4,852,189 | 8/1989 | Duggan | 2/252 |
| 4,879,770 | 11/1989 | Vacilotto | 2/441 |
| 4,918,753 | 4/1990 | Mermillod | 2/10 |

FOREIGN PATENT DOCUMENTS

| | | | |
|---|---|---|---|
| 561597 | 8/1958 | Canada | 2/443 |
| 735281 | 5/1943 | Germany | 2/452 |
| 837004 | 4/1952 | Germany | 2/453 |

*Primary Examiner*—Peter Nerbun
*Attorney, Agent, or Firm*—John J. Swartz

[57] ABSTRACT

A set of goggles comprising a lens holder including a pair of confronting straps having aligned lens apertures therein which receive lens. The straps are coupled together along the bottom, side and outer top confronting edges but are separated at a central, upper passage which is wider than the width of each lens but narrower than twice the width of each lens. Mechanism is provided for detachably coupling the lens holder to headgear, such as a helmet or a bandanna, and includes side bands that are coupled to opposite ends of the straps and extend along the sides of the head of a user. The bands can be detachably coupled to complementally formed fasteners provided on the helmet or bandanna. The side bands include forward portions folded over upon themselves and coupled to the ends of the straps. A rotary, side band adjustment bar is mounted on each end of the strap between the folded portions for adjusting the relative vertical positions of the side bands and the straps to adjust the relative pressures exerted by the upper and lower portions of the straps on the face of the user.

8 Claims, 5 Drawing Sheets

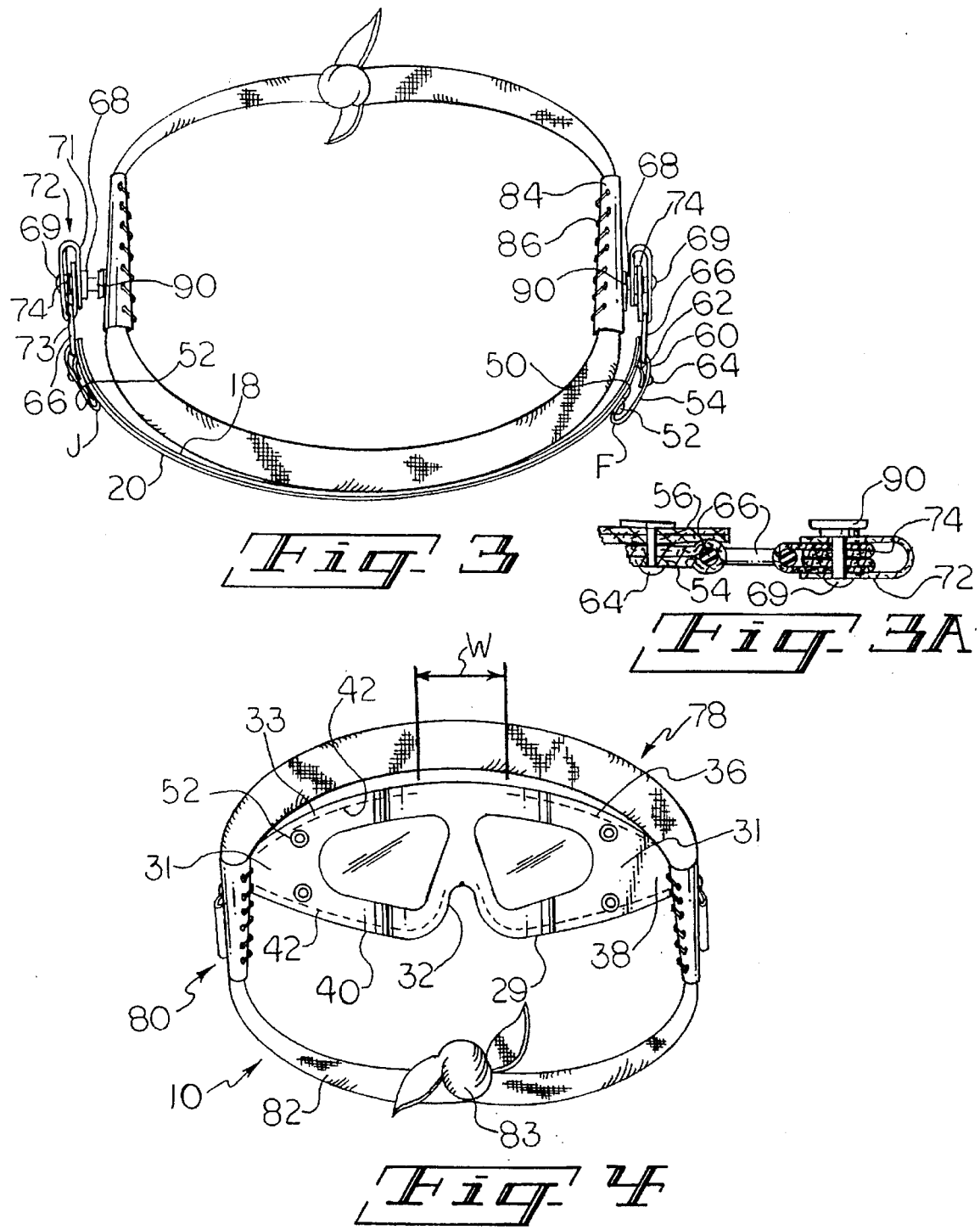

GOGGLES

BACKGROUND OF THE INVENTION

1. Field of the Invention

This invention relates to goggles and more particularly to a lens holder which can be selectively detachably coupled to various headgear and includes a pair of juxtaposed pliable straps defining a lens receiving pocket therebetween and a new and novel centrally disposed upper opening through which a pair of individual eyeglass lens can individually pass to and from positions in the pocket.

2. Description of the Prior Art and Objects

Motorbike operators typically wear goggles to protect their eyes when riding a motorbike. One such set of goggles is illustrated in U.S. Pat. No. 304,835 issued to Robert A. Hodges, on Nov. 28, 1989. This prior art set of goggles included a pair of straps which were coupled together along the bottom and side edges but open along substantially the entire upper border for receiving a pair of lens. Upon removal of the prior art set of goggles from a position covering the biker's eyes, the lens were easily inadvertently separated from the prior art lens holder. Accordingly, it is an object of the present invention to provide a new and novel set of goggles which include a lens holder that will better secure the lens than did the prior art lens construction.

It is another object of the present invention to provide a set of goggles including a pair of straps which are coupled together at their sides, bottom and upper outer edges but are separated at a central, upwardly opening, upper opening which receives the individual eye glass lens that pass to and from a pocket disposed between the straps.

It is yet another further object of the present invention to provide a set of goggles of the type described having an upper central lens receiving opening which is at least as wide as the width of one of the lens but not greater than twice the width of the lens.

Motorbike riders sometimes wear helmets and sometimes wear bandannas. With the prior art lens holder illustrated in the aforementioned patent, it is difficult to wear the lens in combination with a helmet and/or a bandanna. Accordingly, it is a further object of the present invention to provide a set of goggles of the type described which can be selectively coupled and decoupled to and from a helmet and/or a bandanna.

The goggles constructed according to the present invention, include a pair of flexible confronting straps which conform to the contour of a user's face. Some individuals prefer a tighter fit of the lens holder to the face while others prefer a looser fit. Moreover, some individuals prefer that the lens holder be held tighter against the forehead than the facial cheeks and others prefer that the lens holder be held tighter against the individual's cheeks than the forehead. With apparatus constructed according to the structure illustrated in the aforementioned patent, no such adjustment provisions are provided. Accordingly, it is an object of the present invention to provide a set of goggles including a lens holder and mechanism for adjusting the relative pressures exerted by the upper and lower portions of the the lens holder on the user's face.

A still further object of the present invention is to provide a set of goggles of the type described including pressure adjustment mechanism for varying the amount of pressure exerted on forehead and cheeks of a person's face by the lens holder.

Another object of the present invention is to provide a set of goggles of the type described which includes side bands having front portions that are folded over on themselves and rear portions for mounting the lens holder to various headgear.

A further object of the present invention is to provide goggles of the type described including a rotary bar mounted on the ends of a lens holder and bearing against a portion of the side band for adjusting the relative vertical positions of the side bands and the lens holding straps to regulate the amount of pressure exerted by the lens holder on the user's face.

A still further object of the present invention is to provide a lens holder of the type described including new and novel apparatus for coupling the lens holder to a bandanna.

Other objects and advantages of the present invention will become apparent to those of ordinary skill in the art as the description thereof proceeds.

SUMMARY OF THE INVENTION

A set of goggles comprising: a lens holder including a pair of confronting straps each including upper and lower borders spanned by laterally spaced apart side borders; the laterally spaced apart side borders, the lower borders and the laterally outer border portions are secured together to define a lens receiving pocket between the confronting straps, a pair of laterally spaced apart lens passages, of a predetermined width, are provided in each strap laterally inwardly adjacent the side borders and aligned with the laterally spaced apart lens passages in the other strap; a pair of individual lens each having a width greater than the predetermined width, are sandwiched between the straps in alignment with the aligned passages; the upper confronting borders include laterally outer confronting edge portions which are secured together and central confronting edge portions between the laterally outer edge portions define a lens receiving opening in communication with said lens receiving pocket; the lens receiving opening is of a width greater than the predetermined width of one of the lens but less than twice the predetermined width to allow the lens to be removed.

DESCRIPTION OF THE DRAWINGS

The invention may be more readily understood by referring to the accompanying drawings, in which:

FIG. 3 is a top plan view thereof;

FIG. 3a is a greatly enlarged sectional plan view taken along the line 3a—3a of FIG. 2;

FIG. 4 is a rear elevational view thereof;

DESCRIPTION OF PREFERRED EMBODIMENT

Figure 5:
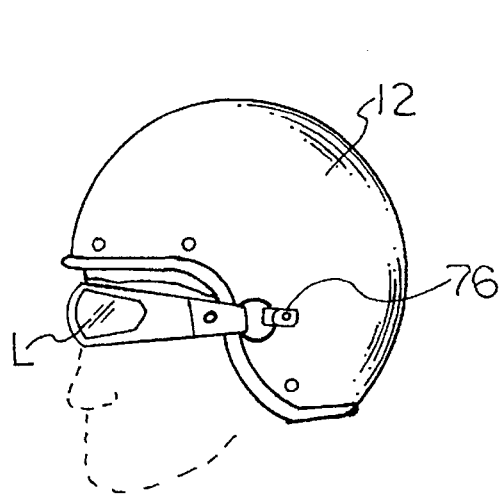
FIG. 5 is a slightly reduced side elevational view illustrating goggles according to the present invention mounted on a biker's helmet.
Figure 6:
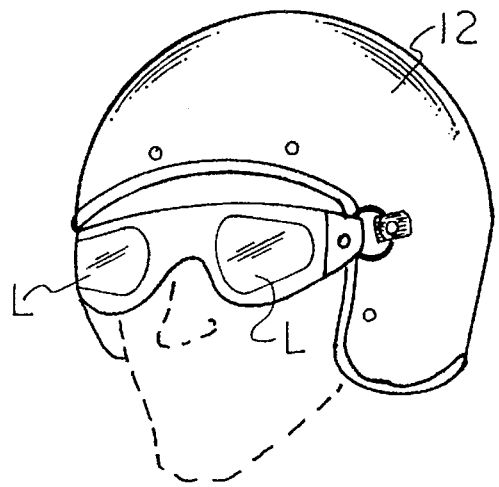
FIG. 6 is a slightly reduced front perspective view of the goggles constructed according to the present invention mounted on a helmet.
Figure 7:
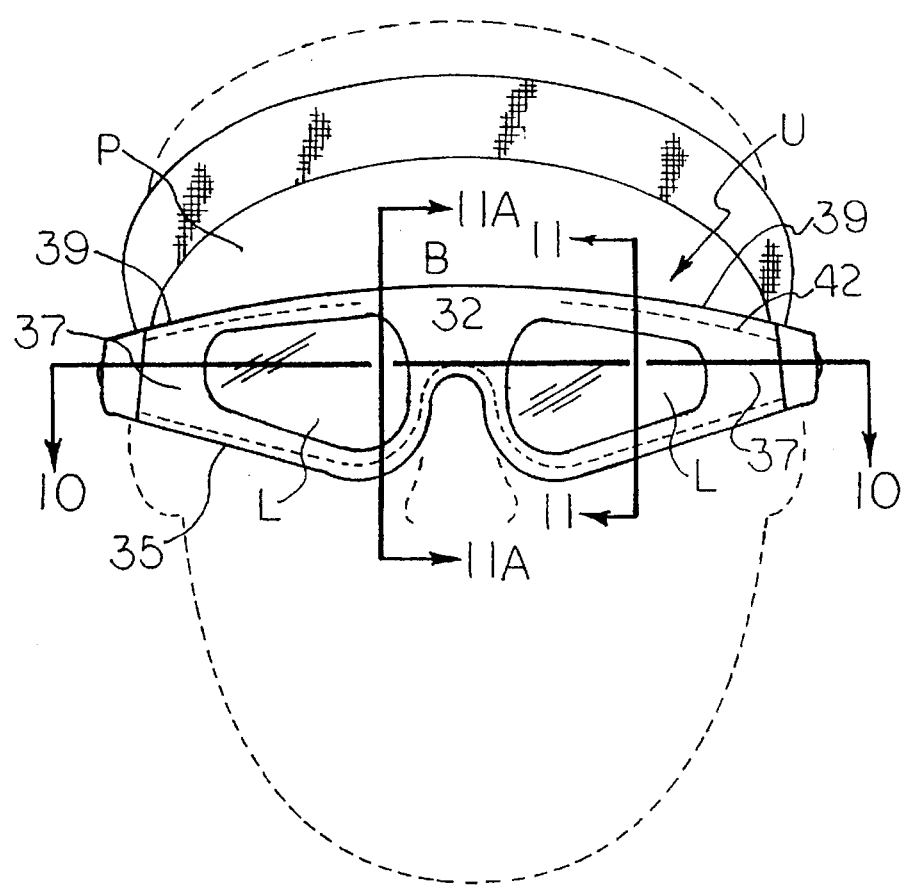
FIG. 7 is a front view illustrating the goggles constructed according to the present invention mounted on a bandanna, the person's head being illustrated in phantom.
Figure 8:
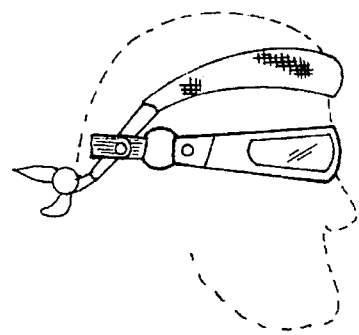
FIG. 8 is a reduced side elevational view, taken from the left side of FIG. 7.
Figure 9:
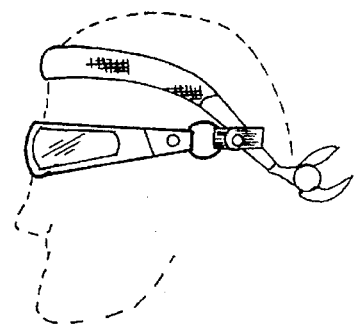
FIG. 9 is an opposite side elevational view of FIG. 7.

The set of goggles, generally designated 10, constructed according to the present invention is particularly adapted for use on a helmet, generally designated 12 (FIG. 5), or a head band, such as a bandanna 14.

The set of goggles 10 includes a lens holder, generally designated 16, including a pair of substantially identical inner and outer straps 18 and 20 having pairs of substantially identical, aligned lenses apertures 19 and 21, respectively.

Figure 10:
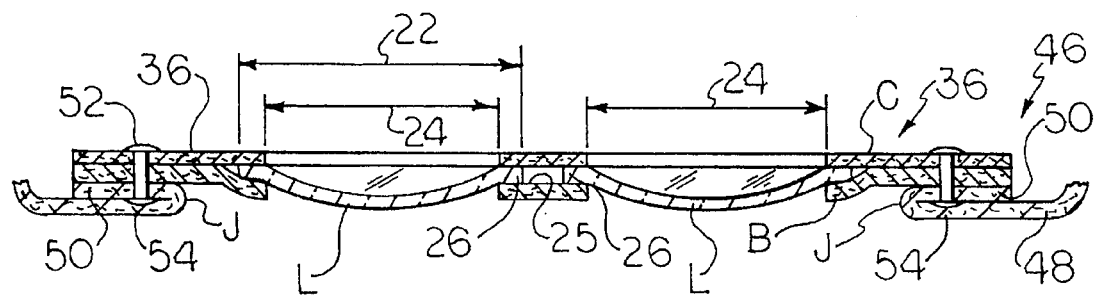
FIG. 10 is a sectional plan view taken along the line 10—10 of FIG. 7.

A pair of lens 23 is received in a pocket 25 provided between the straps 18 and 20 and are disposed in alignment with the pairs of aligned lens apertures 19 and 21. The width 22 (FIG. 10) of each lens 23 is greater than the width 24 of either of the apertures 19 and 21 so that the lens perimeters 26 are sandwiched between the adjacent strap borders B and C surrounding the apertures 19 and 21, respectively. The central lens portions L of one lens 23 is aligned with each set of aligned apertures 19 and 21.

Figure 11:
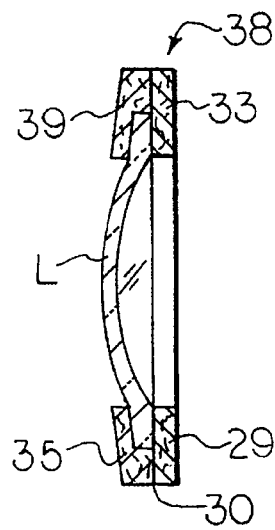
FIG. 11 is a sectional end view taken along the line 11—11 of FIG. 7.
Figure 11A:
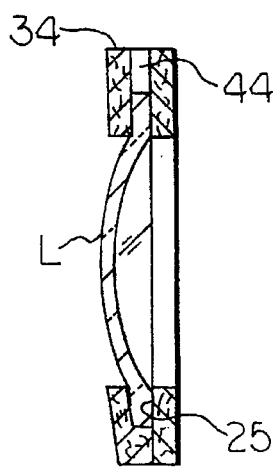
FIG. 11a is a sectional end view taken along the line 11a—11a of FIG. 7.

The inner and outer straps 18 and 20 may be fabricated from many suitable pliable material such as leather. The inner strap 18 includes a lower border portion 29 (FIG. 11), a pair of laterally spaced apart side border portions 31 (FIG. 10) and laterally outer, upper border portions 33 coupled via stitching 42, to the abutting lower border portion 35, laterally spaced border portions 37 and laterally outer upper border portions 39, respectively, of abutting strap 20 to provide a lower solid border 30, laterally outer, solid side or end borders 36 (FIG. 10) and upper, laterally outer solid border portions 38, respectively. The lower border 30 includes a nose receiving cut out 32 for receiving the user's nose. With the exception of the upper central border portion 34, the entire remaining confronting borders 30, 36 and 38 are coupled together via stitching, schematically designated 42. As is clearly illustrated, the lens apertures 19 and 20 extend laterally inwardly of the adjacent strap side borders 38.

The upper border U of the lens holder 16 includes the laterally outer, upper coupled, border portions 33,39 on laterally opposite sides of upper unstitched confronting border portions 43 and 45 of straps 18 and 20, respectively, provide a lens receiving opening or pocket 44 in communication with the opening or pocket 25 between the straps 18 and 20 to allow the lens 23 to pass to and from the pocket 25.

A pair of side bands, generally designated 46, is coupled to opposite border ends 38 of the lens holder 16 and each side band includes a pliable leather strap, generally designated 48, having a forward terminal end 50 which is coupled to a lens holder end 38 via rivets 52 or the like. The adjacent, integral, forward strip portion 54 is integral with, but folded over, the forward terminal strip end 50 to form a pliable fold or junction J. The strip 48 has rearwardly converging upper and lower side edges 56 and 58. The rearward terminal portion 60 of side strip 48 is folded over on the adjacent rearward strap portion 62 and secured thereto via a rivet 64 for receiving a front portion of a coupling ring 66.

Figure 1:
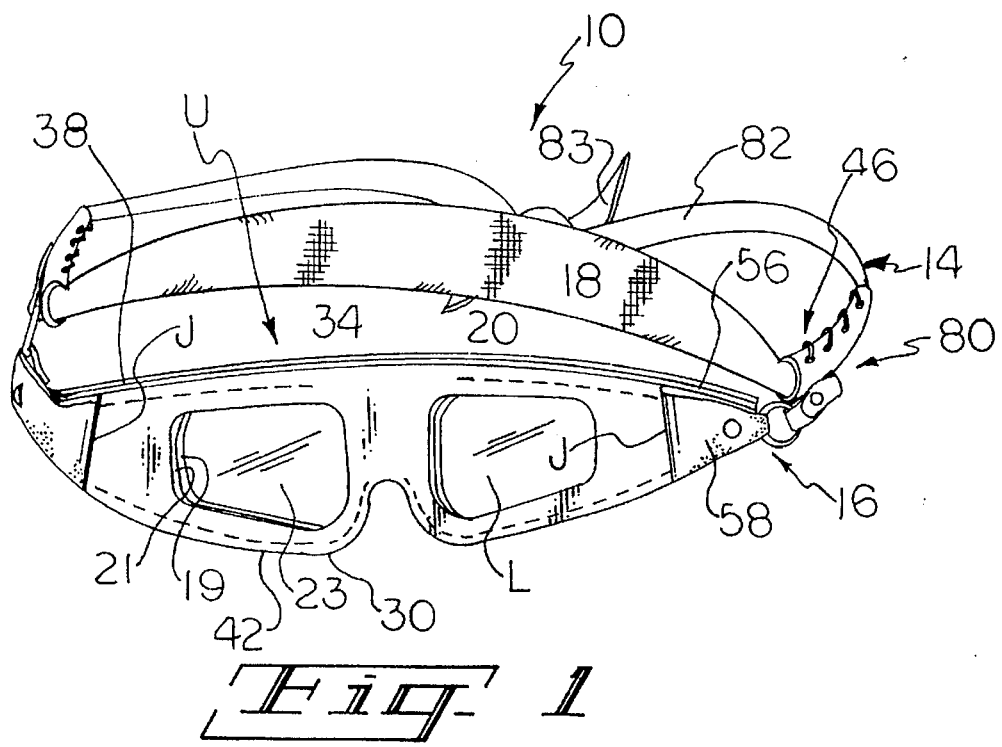
FIG. 1 is a front perspective view of goggles constructed according to the present invention mounted on a bandanna.
Figure 2:
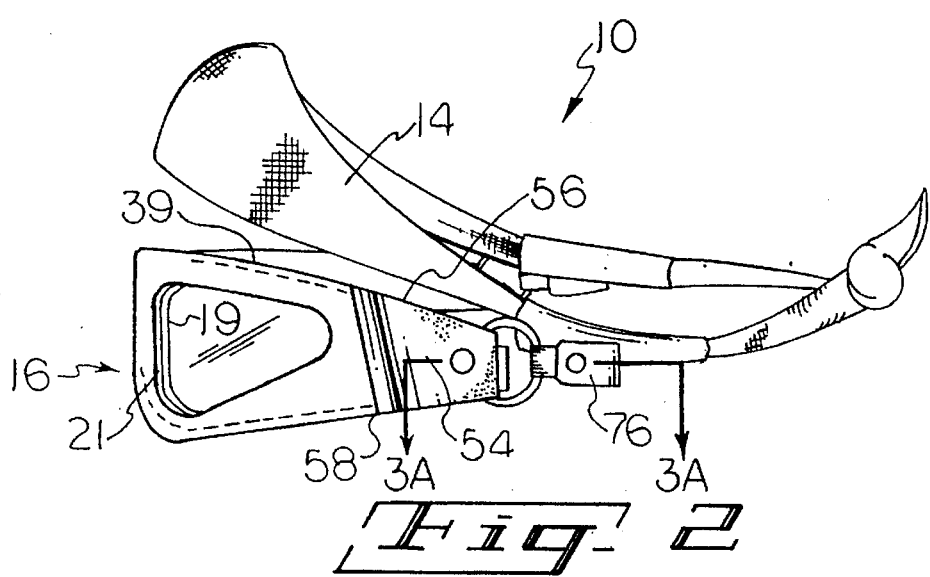
FIG. 2 is a side elevational view thereof.

The side band 46 includes a U-shaped, leather fastener mount 72 having a base 73, which receives the rear portion of coupling ring 66, and a pair of integral legs 71. A female metal fastener 68 is mounted on the inside 70 of fastener mount 72 and includes an integral stud or rivet 69 which fastens together the legs 71 of fastener mount 72. Sandwiched between the legs 71 of fastener mount 72 is a U-shaped elastic band 74 mounted on the rivet 69 and coupled to rear portion of the coupling ring 66. When mounted on a helmet, such as that designated 12 (FIG. 2), the female fasteners 72 are detachably coupled to complimentally formed male fastener 76 provided on opposite sides of the helmet 12.

The bandanna 14 typically comprises a large handkerchief which is folded or rolled over on itself several times and includes a forward portion 78 that is placed against the user's forehead P, side portions 80 which extend along the sides of the head H, and rear portions 82 which are tied in a knot 83 behind the biker's head. To mount the goggles 10 on the bandanna 14, a tubular leather sleeve or sheath 84 is snugly mounted in sliding engagement on the bandanna sides 80 and includes a tie 86 for tying the adjacent sheath ends of sheath 84.

Mounted on the outside 88 of the sheath is a male fastener 90 which is complimental in shape to the female fastener 68 and identical to the helmet mounted, male fasteners 76. The sleeve or sheath 84 snugly receives the bandanna sides 80 but can be slid therealong to adjust the pressure applied to the elastic band 74 and side strips 48 and hence cause the lens holder 16 to more firmly press the lens holder against the user's forehead F.

The side bands 46 thus includes a pliable leather strip 48 having a front terminal end 50, and an integral side strip portion 53 having a forward end 54 integral with and overlying the front terminal end 50 and having vertically spaced upper and lower edges 56 and 58 which rearwardly converge to a rear end 60 that is folded over on itself and riveted at 64. As the tubular sheath 84 is moved rearwardly on the bandanna sides 80, the elastic bands 74 will stretch and exert rearwardly directed pressure, via elastic bands 74 and side bands and strips 48 on the lens holder 16 against the face of the user.

Figure 12:
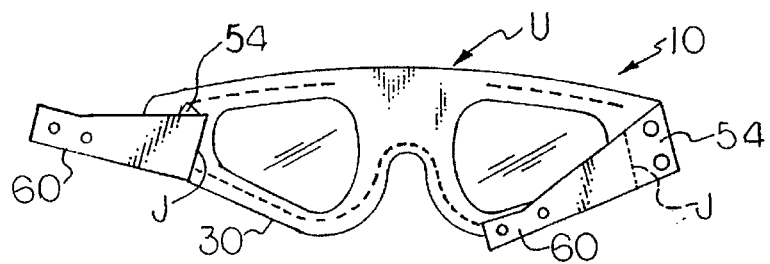
FIG. 12 is a rear elevational view illustrating the side bands in one position of adjustment to apply increased pressure by the bottom border of the lens holder on a person's face.

The junction J of the front terminal end 50 and the adjacent integral portion 54 is flexible and can be adjusted by vertically moving the rear free strip portion 60 relative to the forward fixed strip end 50. By doing so, the amount of pressure exerted by the side bands 46 on the upper border U and lower border 30 will change. For example, if the rear strip ends 60 are moved downwardly to the positions illustrated on the right half of FIG. 12, then more force and pressure will be exerted on the face by the lower border portion 30 than the upper border portion U. On the other hand, if the rear strip ends 60 of the strip are moved vertically upwardly relative to the fixed forward ends 54 to the positions illustrated in the left half of FIG. 12, more force and pressure will be exerted on the biker's face by the upper border U than the lower border 30.

THE OPERATION

The goggles 10 may be mounted on a helmet 12 by snapping the female fasteners 68 on the male fasteners 76 of helmet 12 or to the bandanna 14 by snapping the female fasteners 76 to the male bandanna fasteners 90. If the device is mounted on the bandanna male posts 90, additional rearwardly directed force may be rearwardly applied to the lens holder 16 to make it more tight fitting to the user's face by rearwardly moving the sleeves 84 on the bandanna sides 80.

Figure 13:
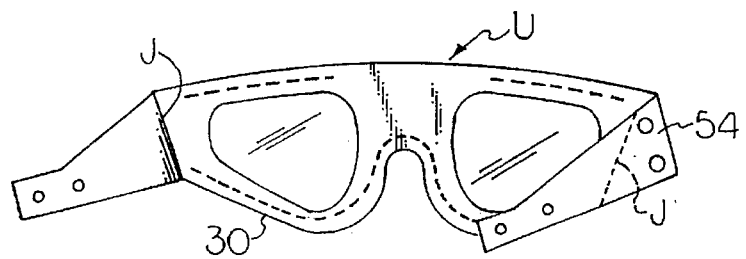
FIG. 13 is a similar rear elevational view illustrating the side bands in an elevated position of adjustment relative to the lens holder to cause increased pressure to be exerted on a user's face by the upper border of the lens holder.

The user can adjust the amount of pressure exerted by the upper and lower lens holder borders U and 30, respectively, by adjusting the attitude of the side strips 48 relative to the lens holder 16. By vertically adjusting or moving the leather side strips 48 and fold junction J to the positions illustrated in FIG. 12, more pressure will be added to the lower border 30 whereas by moving the side strips 48 and fold junctions J to the positions illustrated in FIG. 13, more force will be added to the upper border portion U.

ALTERNATE EMBODIMENT

Figure 14:
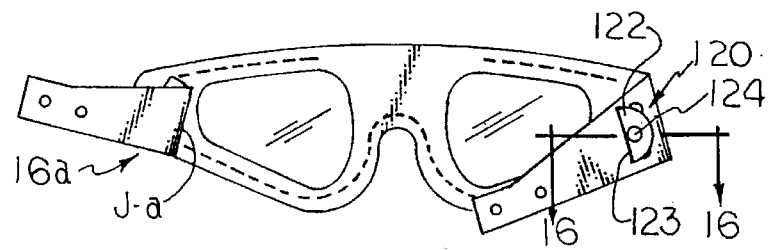
FIG. 14 is a rear elevational view of a slightly modified embodiment including pressure adjustment mechanism illustrated in one position of adjustment.
Figure 15:
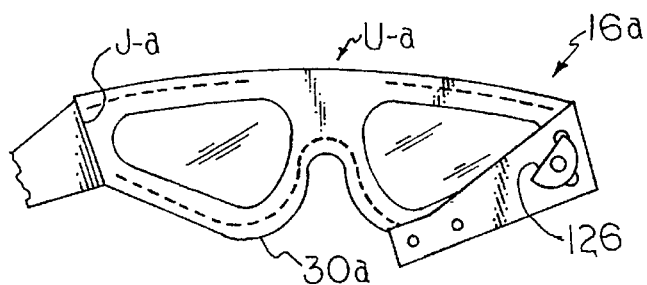
FIG. 15 is a rear perspective view similar to FIG. 14 illustrating the tension adjustment mechanism in an adjusted position.
Figure 16:
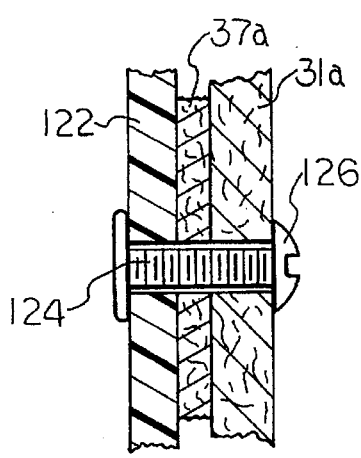
FIG. 16 is an enlarged sectional plan view taken along the line 16—16 of FIG. 14.

Referring now more particularly to FIG. 14–16, a slightly modified construction is illustrated. Generally similar parts will be identified by generally similar reference characters followed by the letter a subscript.

Tension adjustment apparatus, generally designated 120, is provided and includes a pair of side band pressure adjustment bars 122 pivotally mounted on a pair of posts 124 received in an opening provided in the abutting strap end portions 31a, 37a of the lens holder 16a. Each post is threaded into a complimentally formed threaded nut 126 which can be tightened to preclude the bar 122 from rotating or unthreaded from the nut 126 to release pressure on the bar 122 to allow it to rotate. By adjusting the pressure on the bar 122, the bar 122 can be held in any one of a plurality of different rotary positions. The bar 122 will positively hold the side strips 48 in any selected one of a plurality of different vertical positions.

The bar 122 is illustrated as having a half moon shape with a straight edge 123 that bears against the strip junction J-a. If the half moon bar member 122 is rotated to the position illustrated in FIG. 14, then additional force and pressure will be exerted on the biker's face by the top border portion U-a of the lens holder 16a. On the other hand, if the half moon members 122 are moved to the positions illustrated in FIG. 15, then the side strips 48a will cause additional force and pressure to be exerted on the user's face by the lower border 30a.

By partially unthreading nut 126 to release the clamping force on the pressure adjustment bar 122, the bar 122 can be easily rotatably adjusted about the post 124 to the selected position, such as that illustrated in FIG. 15. The nut 126 is again turned on the post 124 to threadedly return the nut 126 to a clamping position in which the pressure adjustment bar 122 is tightly clamped to the adjusted position to hold the fold junction J-a, and thus hold the side bands 46a in the position illustrated at the left side of FIG. 15.

It is to be understood that the drawings and descriptive matter are in all cases to be interpreted as merely illustrative of the principles of the invention, rather than as limiting the same in any way, since it is contemplated that various changes may be made in various elements to achieve like results without departing from the spirit of the invention or the scope of the appended claims.

What I claim is:

1. A set of goggles comprising:

a lens holder including a pair of confronting straps each including upper and lower borders spanned by a pair of laterally spaced apart side borders;

a pair of laterally spaced apart lens apertures, each of a predetermined width, laterally inwardly adjacent said side borders and aligned with the laterally spaced apart aperture in the other strap;

border securing means for securing portions of said borders together to define a lens receiving pocket between said straps in communication with said lens opening including means securing said laterally spaced apart side borders of each strap to the laterally spaced apart borders of the other strap;

means securing said lower confronting borders of said pair of straps together; and means securing laterally outer, upper confronting edge portions of said pair of straps together;

a pair of individual lenses, each having a width greater than said predetermined width, detachably received in said pocket, said lenses each having perimetrical portions sandwiched between said straps, and disposed in alignment with said aligned apertures;

said upper borders being disposed in confronting relation with each other and including said laterally outer, upper confronting edge portions, and upper central edge portions, between said upper confronting edge portions, defining a lens receiving opening in communication with said pocket;

said lens receiving opening having a width greater than said predetermined width of one of said lens but less than twice said predetermined width to allow said lens to be inserted into and removed from said pocket.

2. The set of goggles set forth in claim 1 including attaching means for detachably securing said lens holder to head gear for mounting on a person's head.

3. The set of goggles set forth in claim 2 wherein said attaching means comprises a head band and means for detachably coupling said lens holder to said head band.

4. The set of goggles set forth in claim 2 wherein said attaching means comprises a pair of side bands coupled to said side borders.

5. The set of goggles set forth in claim 4 wherein each of said side bands includes one end attached to one of said side borders and folded on itself, and a free terminal end having a detachable coupling member for coupling to head gear.

6. The set of goggles set forth in claim 5 including pressure adjustment means mounted on said side borders and adjustable to any one of a plurality of different positions to adjust the attitude of the side bands relative to the lens holder.

7. The set of goggles set forth in claim 6 wherein said pressure adjustment means includes means pivotally mounted on said side borders.

8. The set of goggles set forth in claim 7 wherein said pressure adjustment means including a plate, means pivotally mounting said plate for movement about an axis to any one of a plurality of different positions relative to said side border, and means for detachably securing said plate in any one of said plurality of different portions.

* * * * *